(12) United States Patent
Apffel, Jr. et al.

(10) Patent No.: US 6,379,889 B1
(45) Date of Patent: Apr. 30, 2002

(54) MULTIPLEXING METHODS FOR IDENTIFYING NUCLEIC ACIDS USING DENATURING LIQUID CHROMATOGRAPHY

(75) Inventors: James A. Apffel, Jr., Mountain View; Karen M. Hahnenberger, Cupertino; Mel N. Kronick, Palo Alto; Martin Verhoef, Redwood City, all of CA (US)

(73) Assignee: Agilent Technologies, Inc., Palo Alto, CA (US)

( * ) Notice: Subject to any disclaimer, the term of this patent is extended or adjusted under 35 U.S.C. 154(b) by 0 days.

(21) Appl. No.: 09/434,035

(22) Filed: Nov. 4, 1999

(51) Int. Cl.[7] ................ C12Q 1/68; G01N 33/00; C07H 21/02

(52) U.S. Cl. ................ 435/6; 435/6; 436/94; 436/172; 436/800; 436/805; 536/23.1; 536/24.3; 536/25.3

(58) Field of Search .......... 435/6, 91.1, 91.2, 435/183; 536/23.1, 24.3, 24.33, 25.3; 436/94, 800, 805, 172

(56) References Cited

U.S. PATENT DOCUMENTS

| | | | |
|---|---|---|---|
| 4,683,195 A | 7/1987 | Mullis et al. | |
| 4,811,218 A | 3/1989 | Hunkapiller et al. | |
| 5,171,534 A | 12/1992 | Smith et al. | |
| 5,741,411 A | 4/1998 | Yeung et al. | |
| 5,789,153 A | * 8/1998 | Falkner et al. ............... | 435/5 |
| 5,795,976 A | 8/1998 | Oefner et al. | |
| 5,994,076 A | * 11/1999 | Chenchik et al. ............ | 435/6 |

FOREIGN PATENT DOCUMENTS

| WO | WO 97/27325 | 7/1997 |
|---|---|---|

OTHER PUBLICATIONS

O'Donovan et al., "Blind Analysis of Denaturing High–Performance Liquid Chromatography as a Tool for Mutation Detection," Genomics, (1998) vol. 52, pp.44–49.*

Liu et al., "Denaturing high performance liquid chromatography (DHPLC) used in the detection of germline and somatic mutations," Nucleic Acids Research, (1998) vol. 20, pp. 1396–1400.*

Hahnenberger et al., "Applications of HPLC for DNA Analysis," Microbial & Comparative Genomics 3(3), Abstract B–01(1998), and copy of the Poster.

Hewlett–Packard Company product literature, "Zorbax Columns—Eclipse dsDNA," Copyright 1998.

Hewlett–Packard Company product literature, "Zorbax Eclipse dsDNA Analysis Column," Copyright 1999.

Liu et al., "Denaturing High Performance Liquid Chromatography (DHPLC) Used in the Detection of Germline and Somatic Mutations," Nucleic Acids Research, 26(6), 1369–1400 (1998).

O'Donovan et al., "Blind Analysis of Denaturing High–Performance Liquid Chromatography as a Tool for Mutation Detection," Genomics, 52, 44–49 (1998).

Oefner et al., "High–Resolution Liquid Chromatography of Fluorescent Dye–Labeled Nucleic Acids," Analytical Biochemistry, 233, 39–46 (1994).

Oefner, "HPLC in Genetics" abstract from International Symposium on Proteins, Peptides and Polynucleotides meeting registration materials (Nov. 11, 1999).

Oefner et al., "Comparative DNA Sequencing by Denaturing High–performance Liquid Chromatography (DHPLC)," Am. J. Hum. Genet. 57(4), Abstract 1547 (1995).

Ophoff et al., "Familial Hemiplegic Migraine and Episodic Ataxia Type–2 Are Caused by Mutations in the CA2+ Channel Gene CA CNL1A4," Cell, 87(3), 543–552 (1996).

Sarasep, Inc., product literature, "DNASep Startup, Upgrade and Installation Kits—Accessories and Kits for Your HPLC System, to Insure Optimal DNA Analysis" (1995).

Transgenomic, Inc., advertisement, "Analysis of Tumor Heterogeneity at the DNA Level by Automated Fluorescence TMHA Method," copyright 1999.

Transgenomic, Inc., website, "Press: New Wave HS DNA Analysis System Introduced at AACR '99," Jan. 11, 2000.

Transgenomic, Inc., website, "Products & Technology: Nucleic Acid Separations—DHPLC Technology," Jan. 11, 2000.

Verpy et al., "Efficient Detection of Point Mutations on Color–Coded Strands of Target DNA."0 Proc. Natl. Acad. Sci., USA, 91, 1873–1877 (1994).

Wagner, et al., "BRCA 1–Related Breast Cancer in Austrian Breast and Ovarian Cancer Families: Specific BRCA 1 Mutations and Pathological Characteristics," Int. J. Cancer, 77, 354–360 (1998).

* cited by examiner

*Primary Examiner*—Bradley L. Sisson (57) ABSTRACT

A method is provided for the separation of nucleic acid samples. The method includes: providing a test mixture of a plurality of nucleic acid samples, wherein each sample is labeled with a spectrally detectable tag; applying the test mixture to a reversed phase solid support; eluting the mixture under partially denaturing conditions; and detecting spectrally resolved signals produced by the nucleic acid samples labeled with the detectable tags.

19 Claims, 1 Drawing Sheet

MULTIPLEXING METHODS FOR IDENTIFYING NUCLEIC ACIDS USING DENATURING LIQUID CHROMATOGRAPHY

FIELD OF THE INVENTION

The present invention relates to multiplexed chromatographic methods. Such methods can be used for detecting mutations within a population of nucleic acid samples. They can also be used for genotyping and haplotyping.

BACKGROUND OF THE INVENTION

Deciphering the genetic code and the establishment of the structure of deoxyribonucleic acid (DNA) in the early 1960s initiated a revolution in modem biology. Since that time, numerous methods have been developed for the isolation, analysis, and manipulation of nucleic acid samples.

One such method developed for the analysis of nucleic acid samples is polymerase chain reaction amplification (referred to herein as "PCR"). PCR is an in vitro method for replicating a defined (or target) DNA molecule to increase the amount of total DNA for subsequent analysis, such as sequencing, Northern and Southern hybridizations, and the like. Typically, the amount of total DNA increases exponentially, i.e., it is amplified. Thus, PCR can be utilized in connection with a variety of techniques when it is desirable to manipulate and analyze genetic information of a DNA molecule that may be in low copy numbers. For example, PCR may be used in connection with cloning genes, sequencing, genome mapping, site directed mutagenesis, diagnostic assays, environmental monitoring, to name a few.

Due to the vast amount of genetic information that is capable of being generated and gathered, intense efforts are underway to develop new and faster methods of DNA detection, sizing, quantification, sequencing, and gene identification including the mapping of human disease genes. Although the efficiency of these processes has been improved by automation, more efficient and less expensive methods must still be developed to efficiently carry out genomic-scale DNA analyses.

The detection of polymorphisms is becoming increasingly important, particularly in gene mapping. Although the majority of DNA in higher organisms is identical in sequence among the chromosomes of different individuals, a small fraction of DNA is variable or polymorphic in sequence. It is this variation which is the essence of genetic science and human diversity. Mutations arise either due to environmental effects or randomly during replication as a change in the sequence of a gene, with different mutations having differing consequences. In fact, single base pair changes, called single nucleotide polymorphisms (SNPs) are frequent in the human genome. The level of genetic variation between two individual sequences is estimated to be on average one difference per 1,000 base pairs. Based on this estimate, the average amount of genomic variation between individuals is about 3 million base pairs. It is this normal polymorphism, which provides the basis for some of the emerging gene localization strategies.

As the sequences of greater numbers of genes are identified, the detection of specific polymorphisms in such genes and the correlation to specific diseases can provide an invaluable tool in the screening and detection of diseases. Diagnostic screening methods for polymorphisms are also useful in the detection of inherited diseases in which either a single point mutation or a few known mutations account for all cases (e.g., sickle cell disease). Presently, over 200 genetic disorders can be diagnosed using recombinant DNA techniques. Such techniques have also been used for other purposes, such as for forensic screening.

Presently used methods for screening for polymorphic sites within a gene include single-stranded conformation polymorphism (SSCP), denaturing gradient gel electrophoresis (DGGE), RNase A cleavage, chemical cleavage, allele specific oligonucleotides (ASOs), ligase mediated detection of mutations, and denaturing high performance liquid chromatography.

Briefly, in single-stranded conformation polymorphism (SSCP), DNA is denatured and then immediately run on a non-denaturing gel. The secondary structures of wild-type strands or mutant single strands differing by a single base are usually sufficiently different to result in different migration rates on polyacrylamide gels.

In denaturing gradient gel electrophoresis (DGGE), either homoduplex or heteroduplex double stranded DNA is electrophoresed under denaturing conditions of increasing concentration until the last domain is denatured, and migration of the DNA through the gel is retarded. DNA sequences differing by a single base pair migrate at different rates along the gel, thereby allowing detection of a polymorphic site, if present.

RNase A cleavage utilizes the enzyme ribonuclease A to cut RNA-DNA hybrids wherever there is a mismatch between a nucleotide in the RNA strand and the corresponding nucleotide in the DNA strand. The chemical cleavage method is based upon a similar principle but uses hydroxylamine and osmium tetroxide to distinguish between mismatched C or T nucleotides, respectively. The position of the mismatch (e.g., the mutation) is defined by sizing on gel electrophoresis after cleavage at the reactive position by piperidine.

Allele-specific oligonucleotide probes (ASOs) are probes that are designed to hybridize selectively to either a normal or a mutant allele, where the probes are developed to distinguish between the normal and mutant sequence. This is done by altering the stringency of hybridization to a level at which each of the oligonucleotides will anneal stably only to the sequence to which it is perfectly complementary and not to the sequence with which it has the single mismatch.

The ligase-mediated method for detecting mutations makes use of the fact that the ends of two single strands of DNA must be exactly aligned for DNA ligase to join them. In utilizing this technique, oligonucleotides complementary to the target sequence, 5' to and including the mutation site, are synthesized and labeled. A third oligonucleotide complementary to the common sequence 3' to the mutation site is synthesized and also labeled. The oligonucleotides are then hybridized to strands of the target. In cases in which the 5' and 3' oligonucleotides form a flush junction that can be joined by DNA ligase, ligation occurs. However, a single base pair mismatch occurring between the normal 5' oligonucleotide and the mutation site is sufficient to prevent the ligase from acting and can readily be detected.

A common approach to analysis of DNA polymorphisms relies on variations in the lengths of DNA fragments produced by restriction enzyme digestion. The polymorphisms identified using this approach are typically referred to as restriction fragment length polymorphisms or RFLPs. Polymorphisms involving variable numbers of tandemly repeated DNA sequences between restriction enzyme sites, typically referred to as microsatellites or variable numbers of tandem repeats (VNTRs), have also been identified.

While existing methods may locate polymorphic sites, point mutations, insertions and deletions on a gene, many of these methods are generally time consuming, necessitate multiple handling steps, require product purification, are not readily adaptable to automation, have limitations in sensitivity and accuracy, and are typically limited to detection in small-sized nucleic acid fragments.

Furthermore, existing methods typically do not yield haplotype information (i.e., linked polymorphism) without the use of multiple, and often complicated, steps that may incorporate toxic chemicals. See, for example, Verpy et al., *Proc. Natl. Acad. Sci., USA*, 95, 1873–1877 (1994).

Denaturing high performance liquid chromatography for separating heteroduplex (double-stranded nucleic acid molecules having less than 100% sequence complementarity) and homoduplex (double-stranded nucleic acid molecules having 100% sequence complementarity) nucleic acid samples (e.g., DNA or RNA) in a mixture is described in U.S. Pat. No. 5,795,976 (Oefler et al.). In the separation method, a mixture containing both heteroduplex and homoduplex nucleic acid samples is applied to a stationary reversed phase support. The sample mixture is then eluted with a mobile phase containing an ion-pairing reagent and an organic solvent. Sample elution is carried out under conditions effective to at least partially denature the duplexes and results in the separation of the heteroduplex and homoduplex molecules. Also disclosed is the amplification of homoduplex and heteroduplex molecules using the polymerase chain reaction. The amplified DNA molecules are denatured and renatured to form a mixture of heteroduplex and homoduplex molecules prior to separating the molecules. This method can be used to run multiple samples at once as long as the different samples do not co-elute in time, which is referred to as multiplexing in time. The disadvantage of this is that each analytical run takes longer than a single non-multiplexed run.

SUMMARY OF THE INVENTION

What is yet needed is a relatively rapid method for identifying nucleic acids, specifically for distinguishing individual polymorphic nucleic acid molecules. What is also needed is a relatively rapid method for genotyping and haplotyping that involves relatively fewer steps, is capable of automation, and generates information relatively quickly. The present invention provides such methods. In a preferred embodiment, a method of the present invention can be used to distinguish individual PCR amplicons (also referred to as PCR products herein) from a PCR reaction mixture. Significantly and advantageously, the present invention involves the use of multiplexed denaturing liquid chromatography, particularly multiplexed denaturing high performance liquid chromatography.

As used herein, "multiplexing" or "multiplexed" refers to the ability to run multiple (different) samples substantially simultaneously under similar conditions and be able to reconstruct the data individually for each sample. It involves using a detectable label or tag that can be monitored spectrally. In essence, the method of the present invention involves spectral multiplexing. This is distinct from multiplexing in time because in the present invention all samples can be run in the same time period in which one sample could be run (i.e., substantially simultaneously). In a preferred embodiment of the invention, using fluorescence multiplexing, the samples are exposed to radiation having a wide range of wavelengths, individual wavelengths are monitored, and then the mixed signals, which are spectrally resolved, are reconstructed according to their spectral properties.

In one embodiment of the present invention, a method is provided for separating nucleic acid (e.g., DNA and RNA) samples in a test mixture. The method includes: providing a test mixture of a plurality of nucleic acid samples, wherein each sample is labeled with a spectrally detectable tag; applying the test mixture to a reversed phase support; eluting the mixture under partially denaturing conditions to separate at least one nucleic acid sample from the test mixture (preferably, all of the nucleic acid samples are separated from each other during the elution); and detecting spectrally resolved signals produced by the nucleic acid samples labeled with the detectable tags. Preferably, the nucleic acid samples include PCR products (i.e., PCR amplicons), particularly heteroduplexes and homoduplexes. Preferably, the reversed phase solid support is in a high performance liquid chromatography (HPLC) column.

Preferably, the tag is selected from the group of electromagnetic and electrochemical tags, and more preferably, the tag is selected from the group of spectrophotometric and spectrofluorometric tags, and most preferably, the tag is a spectrofluorometric tag. In a particularly preferred embodiment, the detectable label or tag is a fluorescent dye. Preferably, the test mixture is formed by combining a different fluorescent dye with each nucleic acid sample to form a labeled nucleic acid sample; and combining the labeled nucleic acid samples to form the test mixture. Preferably, a different fluorescent dye is added to each nucleic acid sample separately during polymerase chain reaction amplification of the nucleic acid sample prior to combining the nucleic acid samples to form the mixture.

In the present method, the eluting step includes the use of a mobile phase containing an ion-pairing agent and optionally an organic solvent. Examples of ion-pairing agents include amines such as lower alkyl primary, secondary, and tertiary amines, ammonium salts such as lower trialkylammonium salts (e.g., triethylammonium acetate) and lower alkyl quaternary ammonium salts.

A variety of methods can be used for partial denaturation of the mixture of nucleic acid samples (e.g., PCR amplicons). For example, temperatures of about 50° C. to about 80° C. can be used. Alternatively, a chemical reagent for denaturation can be used in the mobile phase.

Preferably, detecting spectrally resolved signals involves the use of spectrophotofluorometric methods of detection in which excitation and emission wavelengths can be independently chosen. In such methods, emission wavelengths can be detected at very low concentrations, often at less than about 1 nanomolar concentrations. Thus, in preferred embodiments, the methods of the present invention include detecting spectrally resolved signals using a spectrophotofluorometric HPLC detector.

Typically, detecting spectrally resolved signals produced by the nucleic acid samples labeled with the detectable tags includes passing the separately labeled nucleic acid samples through a detection zone of a detector substantially simultaneously, each sample generating a specific signal which is spectrally resolved from the specific signals of the other nucleic acid samples. Preferably, the detector excites the detectable tags at one wavelength and detects emissions at multiple wavelengths. Alternatively, the detector can excite the detectable tags using zero-order excitation.

In one preferred embodiment, the present invention provides a method for detecting genotypic variations. The method includes: providing a pre-mixture that includes one unlabeled nucleic acid sample and two or more reference genotypes of labeled nucleic acid, wherein each labeled nucleic acid is labeled with a different spectrally detectable tag and the unlabeled nucleic acid is present in an excess amount relative to the total amount of labeled nucleic acid; denaturing and reannealing the pre-mixture to form a test mixture comprising labeled/unlabeled nucleic acid duplexes; applying the test mixture to a reversed phase support; eluting the test mixture under partially denaturing conditions to separate at least one of the labeled/unlabeled nucleic acid duplexes from the test mixture; detecting spectrally resolved signals produced by the labeled nucleic acid to define an elution profile for each tag; and deducing from the elution profiles the composition of the unlabeled nucleic acid sample. Preferably, the tag is a spectrally detectable tag selected from the group of an electromagnetic tag and an electrochemical tag.

In another preferred embodiment, the present invention provides a method for determining haplotypes. The method includes: providing a pre-mixture that includes one unlabeled nucleic acid sample and four or more reference haplotypes of labeled nucleic acid, wherein each labeled nucleic acid sample includes two or more alleles, each reference haplotype is labeled with a different detectable tag, and the unlabeled nucleic acid is present in an excess amount relative to the total amount of labeled nucleic acid; denaturing and reannealing the pre-mixture to form a test mixture comprising labeled/unlabeled nucleic acid duplexes; applying the test mixture to a reversed phase support; eluting the test mixture under partially denaturing conditions to separate at least one of the labeled/unlabeled nucleic acid duplexes from the test mixture; detecting spectrally resolved signals produced by the labeled nucleic acid to define an elution profile for each tag; and deducing from the elution profiles the composition of the unlabeled nucleic acid sample. Preferably, the tag is a spectrally detectable tag selected from the group of an electromagnetic tag and an electrochemical tag.

DEFINITIONS

The following terms, as used herein, have the meanings as indicated:

"Reversed phase support" refers to a stationary support (including the base material and any chemically bonded phase) for use in liquid chromatography, particularly high performance liquid chromatography (HPLC), which is less polar (e.g., more hydrophobic) than the starting mobile phase.

"Ion-pair (IP) chromatography" refers to a chromatographic method for separating samples in which some or all of the sample components contain functional groups which are ionized or are ionizable. Ion-pair chromatography is typically carried out with a reversed phase column in the presence of an ion-pairing reagent.

"Ion-pairing reagent" is a reagent which interacts with ionized or ionizable groups in a sample to improve resolution in a chromatographic separation. An "ion-pairing agent" refers to both the reagent and aqueous solutions thereof An ion-pairing agent is typically added to the mobile phase in reversed phase liquid chromatography for optimal separation. The concentration and hydrophobicity of an ion-pairing agent of choice will depend upon the number and types (e.g., cationic or anionic) of charged sites in the sample to be separated.

"Homoduplex molecules" are typically composed of two complementary nucleic acid strands.

"Heteroduplex molecules" are typically composed of two complementary nucleic acid strands (e.g., DNA or RNA), where the strands have less than 100% sequence complementarity. Functionally, in a mixed population of homoduplex and heteroduplex molecules, shorter strands (e.g., typically about less than 50 base pairs in size) of heteroduplex molecules elute as peaks corresponding to their respective denatured single strands under select denaturing conditions using reversed phase ion-pairing chromatography, separable from those of homoduplex molecules. In a mixed population of homoduplex and heteroduplex molecules larger than about 50 base pairs in length, heteroduplex molecules typically elute with shorter retention times than those of homoduplexes of essentially the same size under select denaturing conditions using reversed phase ion-pairing chromatography.

A heteroduplex molecule that is "partially denatured" under a given set of chromatographic conditions refers to a molecule in which several complementary base pairs of the duplex are not hydrogen-bond paired, such denaturing typically extending beyond the site of the base-pair mismatch contained in the heteroduplex, thereby enabling the heteroduplex to be distinguishable from a homoduplex molecule of essentially the same size. In accordance with the present invention, such denaturing conditions may be either chemically (e.g., resulting from pH conditions) or temperature-induced, or may be the result of both chemical and temperature factors.

"Genotype" refers to the genetic constitution of a cell or an organism such that expression of the genetic constitution gives rise to an organism's physical appearance. In general, the genetic constitution means a gene, wherein alternative forms of the gene are called "alleles." Typically, an allele is carried at a genetic locus, or position, on an organism's chromosome. "Genotyping" refers to detecting which alleles are present in a given individual.

"Haplotype" refers to a set of closely linked alleles on a specific chromosome carried by an individual and inherited as a unit, such as the alleles of the major histocompatibility complex on human chromosome number 6. "Haplotyping" refers to detecting a change or mutation that may be within one or all of the linked alleles (i.e., the haplotype).

"Primer" refers to an oligonuleotide, whether occurring naturally as in a purified restriction digest or produced synthetically, which is capable of acting as a point of initiation of synthesis when placed under conditions in which synthesis of a primer extension product that is complementary to a target nucleic acid strand is induced, i.e., in the presence of nucleotides and an agent for polymerization (such as a DNA polymerase) and at a suitable temperature and pH. The primer is preferably single stranded for maximum efficiency in amplification. Preferably, the primer is an oligodeoxyribonucleotide. The primer must be sufficiently long to prime the synthesis of extension products (referred to herein as "PCR products" and "PCR amplicons") in the presence of the polymerization agent. Primers are preferably selected to be "substantially" complementary to a portion of the target nucleic acid sequence to be amplified. This typically means that the primer must be sufficiently complementary to hybridize with its respective portion of the target sequence. For example, a primer may include a non-complementary nucleotide portion at the 5' end of the primer, with the remainder of the primer being complementary to a portion of the target sequence. Alternatively, non-complementary bases or longer sequences can be interspersed into the primer, provided that the primer sequence has sufficient complementarity with a portion of the target sequence to hybridize therewith, and thereby form a template for synthesis of the extension product.

BRIEF DESCRIPTION OF THE FIGURES

FIG. 1 shows the spectra of the fluorescence multiplexed denaturing high performance liquid chromatography (DHPLC) runs of two heteroduplexes.

DETAILED DESCRIPTION OF THE INVENTION

The present invention provides a method for separating nucleic acid samples (DNA and RNA), preferably generated from PCR amplification, using multiplexed denaturing liquid chromatography and more particularly, denaturing high performance liquid chromatography. The method can be utilized for detecting nucleic acid PCR products from multiple amplification reactions, so long as each amplification reaction incorporates an agent having a unique spectral signature, wherein each reaction does not contain the same agent.

The present invention also provides a method for genotyping and haplotyping nucleic acid samples, preferably generated from PCR amplification, using multiplexed denaturing liquid chromatography and more particularly, denaturing high performance liquid chromatography.

Multiplexing refers to a method of analyzing samples substantially simultaneously using some means by which the signals of the individual samples can be reconstructed separately and independently of the others. The advantage of multiplexing is that it allows more samples to be analyzed in the same amount of time, increasing effective sample throughput. For example, if multiple samples, labeled with specific tags are separated simultaneously by chromatographic methods, the elution profile passing through the detector could be separated into the individual original samples by using the detection characteristics of the specific tags to generate specific detection channels.

Multiplexing is significant and advantageous because it addresses the problem of the low throughput of liquid chromatography, particularly DHPLC, by multiplexing the analysis using a detectable label or tag, preferably, a fluorescent dye. Furthermore, in preferred embodiments, use of PCR primers with different tags, such as fluorescent dyes, to amplify nucleic acid from different individuals allows the co-injection during a single run of multiple samples, thereby increasing the throughput of the analysis.

Prior to the method of the present invention, the only method available for multiplexing DHPLC was to co-inject PCR amplicons which are sufficiently different in length to ensure that the peak patterns of the individual samples do not overlap in the chromatogram. This has very limited utility since it only increases the throughput by a factor of two. Furthermore, it is not always possible to predict exactly where different PCR products will elute, especially the split peaks of heteroduplexes.

PCR Amplification and Labeled Primers

PCR amplification involves separating two strands of nucleic acid and annealing oligonucleotide primers to a target nucleic acid molecule and extending the nucleic acid molecule by nucleotide addition from the primers by the action of a polymerase enzyme. The target molecule is defined by 3'- and 5'-flanking nucleic acid portions to which oligonulceotide primers are annealed. The primers are then extended across the target DNA molecule by using a heat-stable polymerase (such as Taq DNA polymerase) in the presence of free deoxynucleoside triphosphates (dNTPs), resulting in a double replication of the starting target nucleic acid molecule.

Preferably, PCR amplification generates PCR amplification products (also referred to as PCR amplicons) incorporating a detectable label or tag. Thus, PCR amplification of target nucleic acid is preferably accomplished by utilizing at least one primer containing a detectable tag. Preferably, each primer utilized in the amplification reaction is labeled with a different spectrally detectable tag. Detectable tags are chosen such that they preferably behave similarly in liquid chromatography. That is, they are chosen such that they are retained on the reversed phase support for substantially the same amount of time. However, such tags also should produce spectrally resolvable signals. This can be accomplished, for example, by selected fluorescent dyes in the same family such as Cy3 and Cy5, which are cyanine dyes, obtained from Amersham-Pharmacia Biotech.

In general, a spectral detection method (i.e., one in which the signal generated can be restricted to a defined subset of a large number of different physical possibilities), preferably an electromagnetic or electrochemical technique, more preferably a spectrophotometric and spectrofluorometric technique, and most preferably, a spectrofluorometric technique, can be used, providing that the following conditions are met. The signals produced by the labeled nucleic acid samples can be resolved with little or no spectral overlap such that the presence of a labeled sample doesn't produce a signal under the detection conditions for other labeled samples. Also, the introduction of different detectable tags does not substantially perturb the denaturation conditions of the nucleic acid samples. That is, introduction of a tag does not cause any significant reduction in the amount of nucleic acid denatured when compared to the amount denatured under the same conditions without the detectable tag. Further, the spectral detection system is amenable to on-line chromatographic detection, and the tags do not substantially perturb the chromatographic retention characteristics of the nucleic acid samples. That is, even with the introduction of a tag the nucleic acid samples show at least partial separation between homoduplexes and heteroduplexes.

For example, ultraviolet, visible, or infrared absorbing tags could be used that would produce specific resolvable ultraviolet, visible, or infrared signals. Alternatively, they may be labeled with tags that are detectable using electrochemical and nuclear magnetic resonance. Nuclear Magnetic Resonance tags could be used that introduce resolvable chemical shifts. Electroactive groups could be used that generate specific resolvable redox signals in amperometic detectors. Mass spectral tags can also be used for certain embodiments, but they are less desired.

Other suitable tags include energy transfer coupled dyes in which primers are labeled with a donor and an acceptor dye. Also, chemiluminescent systems can be utilized which are typically defined as the emission of absorbed energy (typically as light) due to a chemical reaction of the components of the system, including oxyluminescence in which light is produced by chemical reactions involving oxygen.

Examples of a wide variety of tags (a chemical moiety that is used to uniquely identify a nucleic acid of interest) are disclosed in International Publication No. WO 97/27325. These may be covalently bound to the nucleic acid or otherwise associated with the nucleic acid such that they elute simultaneously. If covalently bound tags are used according to the present invention, they are not cleaved prior to the nucleic acid entering the detector.

Preferably, the detectable tag has an excitation and/or emission wavelength. Particularly preferred such tags are fluorescent agents. These are typically dye compounds that emit visible radiation in passing from a higher to a lower electronic state, typically in which the time interval between adsorption and emission of energy is relatively short, generally on the order of about $10^{-8}$ to about $10^{-3}$ second. Suitable fluorescent compounds can include fluorescein, rhodamine, luciferin, as well as a wide variety of others known to one of skill in the art (see, for example, the list of dyes available on the world wide web at "www.apbiotech.com/product/product_index.html" or "www.pebio.com" or "www.probes.com"). The use of fluorescent dyes in the HPLC separation of nucleic acids is disclosed by Oefaer et al., *Anal. Biochem.*, 223, 39–46 (1994).

Denaturing Liquid Chromatography

Liquid chromatography, preferably high performance liquid chromatography (HPLC), generally refers to a technique for partitioning a sample, or more specifically the components of a sample, between a mobile phase (typically containing an ion-pairing reagent) and a stationary phase. In the present invention, a chromatographic method utilizes conditions effective to partially denature duplexes during sample elution to thereby enable the separation and identification of different nucleic acid molecules in a mixture.

Typically, denaturing high performance liquid chromatography is used to identify mutations based on the separation of heteroduplex molecules containing a single base mismatch from homoduplex molecules. As an example, a PCR amplicon from a target sample is mixed with the same amplicon generated from a wild-type reference sample and heated to melt the existing homoduplexes and then allowed to slowly cool resulting in both homo- and heteroduplexes. The HPLC running temperature is chosen such that partial denaturation begins to occur in the area around the polymorphic mismatch. In this partially denatured region, the ion-pairing reagent of the mobile phase, is not able to interact as efficiently between the phosphate backbone and the stationary phase. Thus, heteroduplexes and homoduplexes have different retention times and are separated upon elution.

A variety of methods can be used for partial denaturation of nucleic acid molecules. Elevated temperatures can be used for carrying out the separation method of the invention as long as they are not so high that complete denaturation occurs. Such temperatures are preferably about 50° C. to about 80° C., and more preferably about 55° C. to about 65° C. depending on the specific sequence of the nucleic acid. Alternatively, a chemical reagent for denaturation can be used in the mobile phase. Examples of such chemical reagents include dimethylsulfoxide, urea, formamide, glycerol, and betaine.

Stationary Phase

In the method of the present invention, a test mixture containing a mixture of nucleic acid samples (preferably, resulting from PCR amplification, more preferably, a mixture of heteroduplex molecules and homoduplex molecules) is applied to a stationary phase. Generally, the stationary phase is a reversed phase material (which can include a base material and a chemically bonded phase), which is hydrophobic and less polar than the starting mobile phase (i.e., the starting gradient in a gradient elution mode). A variety of commercially available reversed phase solid supports may be utilized in the present nucleic acid separation method as long as they are able to separate unlabeled nucleic acid molecules.

Reversed phase columns or column packing materials for use in the invention are typically composed of inorganic or organic materials, which may or may not be functionalized, such as silica, cellulose and cellulose derivatives such as carboxymethylcellulose, alumina, zirconia, polystyrene, polyacrylamide, polymethylmethacrylate, and styrene copolymers (e.g., a styrene-divinyl copolymer formed from (i) a styrene monomer such as styrene, lower alkyl substituted styrene (in which the benzene ring contains one or more lower alkyl substituents), alpha-methylstyrene and lower alkyl alpha-methylstyrene and (ii) a divinyl monomer such as $C_4$–$C_{20}$ alkyl and aryl divinyl monomers including divinylbenzene and divinylbutadiene).

A preferred stationary support is a wide pore silica-based alkylated support. The base material composing the solid support is typically alkylated. "Alkylated" as used in reference to the solid support refers to attachment of hydrocarbon chains to the surface of the base material of the solid support. The hydrocarbon chains may be saturated or unsaturated and may optionally contain additional functional groups attached thereto. The hydrocarbon chains may be branched or straight chain and may contain cyclic groups such as cyclopropyl, cyclopropyl-methyl, cyclobutyl, cyclopentyl, cyclopentylethyl, and cyclohexyl.

Alkylation of the base material prevents secondary interactions and can improve the loading of the stationary phase with the ion-pairing reagent to promote conversion of the solid support into a dynamic anion-exchanger. Typically, the base material is alkylated to possess alkyl groups containing at least 3 carbon atoms, generally about 3 to about 22 carbon atoms, and preferably contains about 4 to about 18 carbon atoms. The alkylated solid support phase may optionally contain functional groups for surface modification. The presence or absence of such functional groups will be dictated by the nature of the sample to be separated and other relevant operational parameters.

The stationary phase may also include beads having a particle size of about 1 micron to about 100 microns. As used herein, the particle size is determined by measuring the largest dimension of the particle (typically, the diameter for a spherical particle).

A stationary phase for use in the present method typically has pores with sizes ranging from less than about 30 Angstroms in diameter (e.g., nonporous materials) up to about 1000 Angstroms in size. "Nonporous stationary support" refers to a solid support composed of a packing material having surface pores of a diameter that excludes permeation of sample compounds into the pore structure, typically of less than about 30 Angstroms in diameter. In using nonporous polymeric support materials, the relatively small pore size excludes many sample compounds from permeating the pore structure and may promote increased interaction with the active surface. The stationary phase may also contain more than one type of pore or pore system, e.g., containing both micropores (less than about 50 Angstroms) and macropores (greater than about 1000 Angstroms). For achieving separations of samples containing heteroduplexes and homoduplexes of up to about 1000 base pairs in size, the stationary phase will preferably have a surface area of about 2 $m^2/g$ to about 400 $m^2/g$, and more preferably about 8 $m^2/g$ to about 20 $m^2/g$, as determined by nitrogen adsorption.

Commercially available stationary phases include a wide pore silica-based C18 material commercially available under the trade designation "ECLIPSE ds DNA" from Hewlett Packard Newport, Newport, Del., and an alkylated polystyrene-divinylbenzene nonporous material commercially available under the trade designation "DNASep" from Transgenomic, San Jose, Calif.

Mobile Phase

The separation method of the present invention utilizes denaturing liquid chromatography, preferably denaturing high performance liquid chromatography (DHPLC), and more specifically, ion-pairing reversed phase HPLC (IP-RP-HPLC). In carrying out the separation according to the present method, the aqueous mobile phase contains an ion-pairing agent and a solvent, preferably an organic solvent.

The selection of aqueous mobile phase components will vary depending upon the nature of the sample and the degree of separation desired. Any of a number of mobile phase components typically utilized in ion-pairing reversed phase HPLC are suitable for use in the present invention. Several mobile phase parameters (e.g., pH, organic solvent, ion-pairing reagent and counterion, and elution gradient) may be varied to achieve optimal separation, such as the percent organic solvent, temperature, and concentration of the components.

Ion-pairing reagents for use in the invention are those which interact with ionized or ionizable groups in a sample to improve resolution including both cationic and anionic ion-pairing reagents. Cationic ion-pairing agents for use in the invention include amines such as lower alkyl primary, secondary, and tertiary amines (e.g., triethylamine (TEA)), ammonium salts such as lower trialkylammnonium salts of organic or inorganic acids (e.g., triethylammonium acetate) and lower quaternary ammonium salts such as tetrabutylanmmonium phosphate. Anionic ion-pairing agents include perfluorinated carboxylic acids. Herein, "lower alkyl" refers to an alkyl group of one to six carbon atoms, as exemplified by methyl, ethyl, n-butyl, i-butyl, t-butyl, isoamyl, n-pentyl, and isopentyl.

The hydrophobicity of the ion-pairing agent will vary depending upon the nature of the desired separation. For example, tetrabutylammonium phosphate is considered a strongly hydrophobic cation while triethylamine is a weak hydrophobic cationic ion-pairing reagent. Generally, preferred ion-pairing agents are cationic in nature for acids and anionic for bases. One such preferred ion-pairing agent for use in the invention is triethylammonium acetate (TEAA).

In accordance with the present invention, preferred solvents for use in the mobile phase are organic solvents. The organic solvent, occasionally referred to as an organic modifier, is any organic (e.g., non-aqueous) liquid suitable for use in the chromatographic separation methods of the present invention. Generally, the organic solvent is a polar solvent (e.g., more polar than the stationary support) such as acetonitrile, methanol, ethanol, ethyl acetate, and 2-propanol. A preferred solvent is acetonitrile.

The pH of the mobile phase will vary depending upon the concentrations of various components. For separation of nucleic acid samples such as RNA or DNA molecules, using temperature to effect partial denaturation of the nucleic acid, the pH of the mobile phase is typically maintained within a range of about 7 to about 9. Preferably, the mobile phase is maintained at a pH of about 7.5.

In an alternate embodiment, the pH of the mobile phase is adjusted to effect partial denaturation of the heteroduplex molecules in a mixture of homoduplexes and heteroduplexes to allow separation and detection of the heteroduplex molecules. In using chemical means to effect heteroduplex denaturation, the pH may be adjusted by addition of either base (e.g., sodium hydroxide or urea to a pH of around about 8) or acid (e.g., triethylamine and acetic acid at a pH of about 8) under conditions effective to partially denature the heteroduplex molecules and which do not degrade the nucleic acids present in the sample nor adversely affect the integrity of the stationary phase. In such cases, sample elution may be carried out at temperatures less than about 50° C.

The concentration of the mobile phase components will vary depending upon the nature of the separation to be carried out. The mobile phase composition may vary from sample to sample and during the course of the sample elution. The concentration of the ion-pairing agent in the mobile phase is preferably less than about 1.0 molar, more preferably within a range of about 50 mM to about 200 mM, and most preferably at a concentration of about 100 millimolar. The mobile phase preferably includes less than about 40% by volume of an organic solvent.

Samples are typically eluted by starting with an aqueous or mostly aqueous mobile phase containing an ion-pairing agent and progressing to a mobile phase containing increasing amounts of an organic solvent. Any of a number of gradient profiles and system components may be used to achieve the denaturing conditions of the present invention. One such exemplary gradient system in accordance with the invention is a linear binary gradient system composed of 0.1 molar triethylammonium acetate, 0.1 millimolar ethylenediaminetetraacetic acid (EDTA), and 25% acetonitrile in a solution of 0.1 molar triethylammonium acetate and 0.1 millimolar EDTA. The EDTA is typically used when the reversed phase support is a silica-based material to prevent DNA adsorbing to the silica and/or metal chelation.

One way to achieve the denaturing conditions of the present invention (e.g., effective to partially denature heteroduplexes) is to modulate column temperature. A column temperature typically of about 50° C. to about 65° C. is preferred for resolving heteroduplex molecules from their corresponding homoduplex molecules. The optimal column temperature will depend upon the putative sequence (base composition) of the nucleic acid samples to be separated and the particular detectable tag. Thus, the choice of stationary phase, the choice of mobile phase, pH, flow rate, and the like, and in many cases, will be determined empirically. Ideally, in cases with known sequence, a suitable column temperature may be calculated.

Detection

By incorporating a detectable tag, a mixture containing a plurality of labeled nucleic acid samples can be applied to a first end of a chromatograpy column containing a stationary phase, preferably in the presence of a mobile phase. These samples are run substantially simultaneously through the column under conditions to partially denature the nucleic acid molecules and separate the samples. Upon elution, the nucleic acid species of each of the separately labeled nucleic acid sample pass through the detection zone substantially simultaneously, each sample generating a specific signal which is spectrally resolvable from the specific signals of the other nucleic acid samples. Consequently, each nucleic acid sample generates a chromatogram that can be reconstructed to represent the elution pattern of the individual nucleic acid species in this sample. This chromatogram is distinct and independent of the similarly obtained chromatograms for the other nucleic acid samples that were injected into the system.

A multiwavelength spectral (preferably, fluorescence) detector is preferably operably attached to a second end of the chromatography column. The detector can be used to excite the detectable tags at one wavelength and detect emissions as multiple wavelengths, or excite at multiple wavelengths and detect at one emission wavelength. Alternatively, the sample can be excited using "zero-order" excitation in which the full spectrum of light (e.g., from xenon lamp) illuminates the flow cell. Each compound can absorb at its characteristic wavelength of light and then emit maximum fluorescence. The multiple emission signals can be monitored independently. Preferably, a suitable detector can be programmed to detect more than one excitation emission wavelength substantially simultaneously, such as that commercially available under the trade designation HP1100 (G1321A), from Hewlett Packard, Wilmington, Del. Thus, the labeled nucleic acid samples eluted from the stationary phase can be detected at programmed emission wavelengths at various intervals during elution.

A preferred detector can be programmed to detect at least two, and preferably at least four different excitation or emission wavelengths simultaneously. Thus, PCR products from at least two individuals, each labeled with a different fluorescent tag, can be co-injected, increasing throughput by a factor of at least two. Since the detector has time resolution capabilities, the initial portion of the chromatogram can be scanned for at least two emission wavelengths and the later portion of the chromatogram can be scanned for a second set of at least two emission wavelengths. By combining size of the nucleic acid molecules and fluorescence multiplexing, the throughput of the system can be increased at least 8-fold, e.g., four dyes at two size ranges.

In carrying out the separation method of the present invention, a variety of factors may influence detection resolution. While it is not possible to determine an ideal set of conditions suitable for analyzing all possible nucleic acid fragments by the present method, conditions can be determined empirically to affect detection resolution.

In carrying out the method of the invention, a mixture containing nucleic acid samples (e.g., PCR amplification products) to be analyzed is typically injected and pre-mixed with the mobile phase prior to elution on the solid support. The sample is then contacted directly with the stationary phase, or alternatively, is passed through a "preconditioning" tubing or pre-column to allow the sample and mobile phase to equilibrate before contact with the solid support.

For example, the mobile phase components are introduced into a mixer inside the column oven and mixed prior to contact with the sample. Alternatively, the mobile phase components may be mixed at ambient temperature and contacted with the sample injector, also maintained at ambient temperature outside of the column oven. Additionally, the mixture can be injected into the mobile phase, pre-equilibrated to the temperature of the column. In this manner, a near-direct connection between the column and the injector is provided to minimize diffusion and enhance sample resolution.

Alternately, when utilizing a low-pressure system, sample mixing typically occurs at ambient temperature. In instances in which the autosampler does not provide for heating the injection port to column temperature, standard HPLC tubing (e.g., 0.005-0.01 inch in diameter) may be positioned between the injector and the column, to pre-heat the mobile phase and induce partial denaturation of the DNA sample.

Another factor which affects the parameters to be selected for carrying out the separation method of the invention is the composition of the putative sequence of the PCR amplification products to be analyzed. In this respect, for mixtures containing a polymorphic site flanked by a GC-rich region, higher temperatures may be required to detect the polymorphism.

Genotyping

In genotyping two alleles of a polymorphic site of interest, an exemplary method includes generating two labeled nucleic acid samples (e.g., PCR products) where each of the samples includes one of the putative alleles and a detectable tag, thereby forming reference genotypes. A labeled mixture is formed by mixing the two labeled samples in a ratio of about 1:1. An unlabeled nucleic acid sample (e.g., PCR product) is generated from a sample of interest (e.g., the analyte or unknown entity being evaluated), which contains allele 1 and/or allele 2. A hybrid mixture containing labeled and unlabeled nucleic acid is formed by mixing the labeled mixture with the unlabeled nucleic acid sample. Preferably, the unlabeled sample is present in excess relative to the labeled mixture, preferably, in an excess of at least about 5:1, and more preferably, at least about 10:1.

The hybrid mixture is then denatured and reannealed at temperatures depending on the particular nucleic acids under study (e.g., by heating at a temperature up to about 99° C. for 5 minutes followed by cooling to 45° C. over a period of about 30 minutes). The unlabeled nucleic acid sample is used in excess of the labeled mixture so that one labeled nucleic acid strand preferentially hybridizes to an unlabeled nucleic acid strand rather than to another labeled nucleic acid strand. For the purposes of illustration, the labeled nucleic acid sample (e.g., PCR product) of allele 1 is referred to as "Label 1" and that of allele 2 is referred to as "Label 2." The following table illustrates the combinations that are possible as a result of denaturing and reannealing.

TABLE 1

| Putative Alleles Present in Sample | Result After Reannealing With Unlabeled PCR Product |
| --- | --- |
| Two copies of allele 1 | Label 1 forms only homoduplex |
|  | Label 2 forms only heteroduplex |
| One copy of allele 1 | Label 1 forms both a homoduplex and |
| One copy of allele 2 | heteroduplex |
|  | Label 2 forms both a homoduplex and |
|  | heteroduplex |
| Two copies of allele 2 | Label 1 forms only heteroduplex |
|  | Label 2 forms only homoduplex |

By generating a denaturing liquid chromatogram using the above mixture as a sample and utilizing a fluorescence detector during elution, the genotype can be determined by comparing the results of the elution profiles of each label to the above table.

Haplotyping

The method for genotyping, illustrated above, can be expanded to determine haplotype. For the purposes of illustration, alleles 1 and 2 exist at one polymorphic site and alleles 3 and 4 exist at a second polymorphic site linked to the first. Labeled samples of each haplotype are preferably generated by incorporating a detectable tag such that each of the 4 haplotypes contain a tag having a different detectable signal. As described above, once the 4 labeled samples are obtained, a mixture of the labeled samples is formed. Preferably, they are mixed in a ratio such that the signal (e.g., fluorescent signal) per product is approximately equal. This can be done by adjusting the relative concentration of each sample in the mixture. The sample of interest (analyte) is generated in an unlabeled form. A hybrid mixture including the mixture of labeled samples and the unlabeled sample is formed by mixing the unlabeled sample in a significant excess relative to the labeled samples. Preferably, the ratio of unlabeled to labeled samples is at least about 5:1, and more preferably, at least about 10:1.

The hybrid mixture is then denatured and reannealed at temperatures depending on the particular nucleic acids under study. The unlabeled sample is used in excess of the labeled samples so that each labeled strand preferentially hybridizes to an unlabeled strand rather than to another labeled strand. For the purposes of illustration, assume that the labeled strands contain the haplotypes and the labels listed in the table below.

TABLE 2

| Putative Haplotype | Haplotype Designation | Label in PCR Product |
|---|---|---|
| Allele 1 and Allele 3 | Hap 1 | Label 1 |
| Allele 1 and Allele 4 | Hap 2 | Label 2 |
| Allele 2 and Allele 3 | Hap 3 | Label 3 |
| Allele 2 and Allele 4 | Hap 4 | Label 4 |

Next, using the four labeled reference haplotype samples, the following duplex formation of each haplotype in a sample containing one of the four reference haplotypes can be deduced. In each of the cases where a heterozygote is deduced, a heteroduplex is formed, either with one or two mismatches.

TABLE 3

| Sample Haplotype | Duplex formed with Hap 1 | Duplex formed with Hap 2 | Duplex formed with Hap 3 | Duplex formed with Hap 4 |
|---|---|---|---|---|
| Hap 1 | Homoduplex | Heteroduplex (1 mismatch) | Heteroduplex (1 mismatch) | Heteroduplex (2 mismatches) |
| Hap 2 | Heteroduplex (1 mismatch) | Homoduplex | Heteroduplex (2 mismatches) | Heteroduplex (1 mismatch) |
| Hap 3 | Heteroduplex (1 mismatch) | Heteroduplex (2 mismatches) | Homoduplex | Heteroduplex (1 mismatch) |
| Hap 4 | Heteroduplex (2 mismatches) | Heteroduplex (1 mismatch) | Heteroduplex (1 mismatch) | Homoduplex |

The possible combinations that can result from a sample with either one or two of the four unique haplotypes are summarized in the following table.

TABLE 4

| Sample Haplotype | Duplex formed with Hap 1 | Duplex formed with Hap 2 | Duplex formed with Hap 3 | Duplex formed with Hap 4 |
|---|---|---|---|---|
| Hap 1/Hap 1 | Homoduplex | Heteroduplex (1 mismatch) | Heteroduplex (1 mismatch) | heteroduplex (2 mismatches) |
| Hap 1/Hap 2 | Homoduplex and Heteroduplex (1 mismatch) | Homoduplex and Heteroduplex (1 mismatch) | Heteroduplex (1 mismatch) and Heteroduplex (2 mis-matches) | Heteroduplex (1 mismatch) and Heteroduplex (2 mismatches) |
| Hap 1/Hap 3 | Homoduplex and Heteroduplex (1 mismatch) | Heteroduplex (1 mismatch) and Heteroduplex (2 mismatches) | Homoduplex and Heteroduplex (1 mismatch) | Heteroduplex (1 mismatch) and Heteroduplex (2 mismatches) |
| Hap 1/Hap 4 | Homoduplex and Heteroduplex (2 mismatches) | Heteroduplex (1 mismatch) | Heteroduplex (1 mismatch) | Homoduplex and Heteroduplex (2 mismatches) |
| Hap 2/Hap 2 | Heteroduplex (1 mismatch) | Homoduplex | Heteroduplex (2 mismatches) | Heteroduplex (1 mismatch) |
| Hap 2/Hap 3 | Heteroduplex (1 mismatch) | Homoduplex and Heteroduplex (1 mismatch) | Homoduplex and Heteroduplex (2 mismatches) | Heteroduplex (1 mismatch) |
| Hap 2/Hap 4 | Heteroduplex (1 mismatch) and Heteroduplex (2 mismatches) | Homoduplex and Heteroduplex (1 mismatch) | Heteroduplex (1 mismatch) and Heteroduplex (2 mismatches) | Homoduplex and Heteroduplex (1 mismatch) |
| Hap 3/Hap 3 | Heteroduplex (1 mismatch) and Heteroduplex (2 mismatches) | Heteroduplex (2 mismatches) | Homoduplex | Heteroduplex (1 mismatch) |
| Hap 3/Hap 4 | Heteroduplex (2 mismatches) | Heteroduplex (1 mismatch) and Heteroduplex (2 mismatches) | Homoduplex and Heteroduplex (1 mismatch) | Homoduplex and Heteroduplex (1 mismatch) |
| Hap 4/Hap 4 | Heteroduplex (2 mismatches) | Heteroduplex (1 mismatch) | Heteroduplex (1 mismatch) | Homoduplex |

Because each of the four labeled nucleic acid samples (e.g., PCR products) corresponding to the four reference haplotypes contains a different label, a unique elution chromatographic pattern in each label will be associated with any one of the ten combination haplotypes listed above. Because the unlabeled nucleic acid sample is included in the hybrid mixture in significant excess of the labeled samples, a very small amount of labeled/labeled duplex would be expected to anneal and thus, a very small amount of labeled/labeled duplex is likely to be detected. Additionally, if only one strand of the labeled nucleic acid sample actually includes the label, then only one heteroduplex would be detected rather than two if both strands were labeled. However, it may be advantageous to label both strands of a labeled nucleic acid sample because two different heteroduplexes may be detected, which may provide confirmatory information in the measurement.

EXAMPLES

The objects, features and advantages of the present invention illustrated in the following examples, which incorporate particular materials and amounts, should not be construed to unduly limit this invention. All materials are commercially available unless otherwise stated or apparent. All parts, percentages, ratios, etc., in the examples are by weight unless otherwise indicated.

Figure 1A:
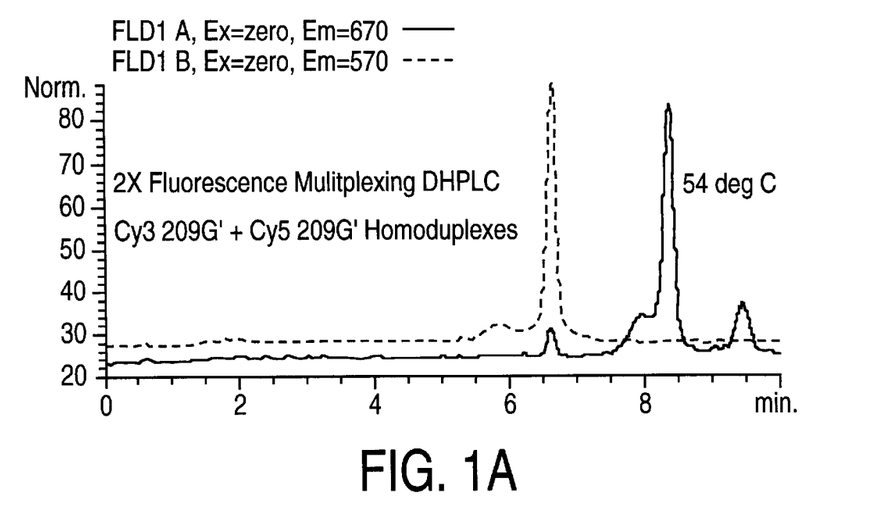
Figure 1B:
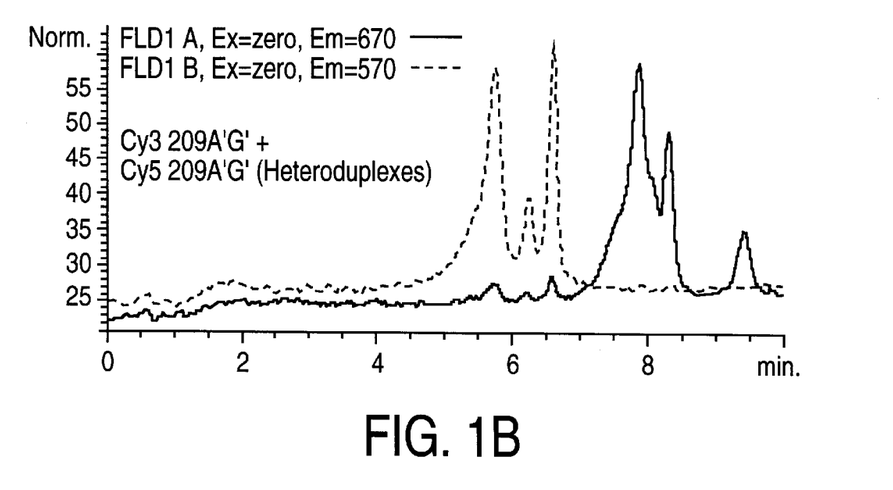

In the spectrum shown in FIG. 1, two samples, each consisting of equal mixtures of a "wild-type" sequence and an A to G variant at sequence position Y were labeled with different fluorescent dyes and analyzed simultaneously by fluorescence multiplexed DHPLC. The individual signals were separated and resolved spectrally. In FIG. 1A, the control homoduplex sample labeled with Cy3 and Cy5 cyan dyes (Amersham-Pharmacia Biotech.) was predominantly two well resolved peaks. In the lower panel (FIG. 1B), test sample consisting of both homo- and heteroduplex samples labeled both Cy3 and Cy5 shows a distinctly different pattern indicating the presence of a polymorphism.

The individual samples were prepared by PCR amplifying the two individual templates (termed 209A and 209G) with one of the PCR primers fluorescently labeled. In one case the primer was labeled with a Cy3 dye (Excitation=550 nm; Emission=570 nm), in the other case the primer was labeled with a Cy5 dye (Excitation=649 nm; Emission=670 nm). Following amplification, the Cy3 labeled 209A and 209G amplicons were mixed in equal proportions and placed in a separate PCR tube. The Cy5 labeled 209A and 209G samples were mixed in equal proportions and placed in a separate tube. These two mixtures were then heat treated to produce mixtures of homo- and heteroduplexes by heating to 99° C. for 5 minutes and gradually cooling to 45° C. over 60 minutes and then held at 4° C. for 90 minutes. The resulting Cy3 and Cy5 labeled homo- and heteroduplex mixtures were then pooled and used for a single simultaneous analysis by fluorescence multiplexed DHPLC.

It should be noted that adding a tag may change the optimal temperature for partial denaturation, so that the operating temperature may need to be adjusted from the predicted value. Also, adding a tag may change the optimal HPLC gradient for resolution, so the separation conditions may need to be adjusted from the predicted value.

All DHPLC analytical analyses were performed using a Hewlett-Packard HP 1100 HPLC with Binary Pump, thermostatted autosamper, thermostatted column oven, Diode Array UV/VIS detector and Fluorescence Detector. This system is unmodified and commercially available except for the addition of an aluminum block around the HPLC column to help maintain constant temperature. The HPLC column consisted of a 75 mm×2.1 mm I.D., 3.5 $\mu$m Eclipse dsDNA column with a guard column. For this particular example, the column temperature was held at 54° C. Mobile phase A consisted of 100 mM triethylammonium acetate, 0.1 mM EDTA. Mobile phase B consisted of 25% acetonitrile, 100 mM triethylammonium acetate, and 0.1 mM EDTA. The initial mobile phase was 45% B at 0.4 ml/minute. Following injection of 2 $\mu$L of sample, the mobile phase gradient ramped mobile phase to 60% B in 0.1 minute followed by a ramp to 80% B in 10 minutes. By this time the samples eluted from the column and the mobile phase was changed to 100% B and held for 1 minute to clean up the column and then reequilibrated at 45% B for 5 minutes. The samples eluting from the column entered the fluorescence detector with a zero-order broad band excitation and emission monitored at 570 nm for Cy3 and 670 nm for Cy5.

Patents, patent applications, and publications disclosed herein are hereby incorporated by reference as if individually incorporated. It is to be understood that the above description is intended to be illustrative, and not restrictive. Various modifications and alterations of this invention will become apparent to those skilled in the art from the foregoing description without departing from the scope and the spirit of this invention, and it should be understood that this invention is not to be unduly limited to the illustrative embodiments set forth herein.

What is claimed is:

1. A method for separating nucleic acid samples in a test mixture using denaturing liquid chromatography, the method comprising the steps of providing a test mixture comprising a plurality of nucleic acid samples, wherein each sample is labeled with a different spectrally detectable tag that produces a different spectrally resolvable signal;

applying the test mixture to a reversed phase support in a denaturing liquid chromatography column;

eluting the test mixture under partially denaturing conditions to separate at least one of the nucleic acid samples from the test mixture, the partially, denaturing conditions being selected from at least one or both of temperature-induced or chemical-induced conditions; and detecting the spectrally resolved signals produced by the nucleic acid samples labeled with the different spectrally detectable tags.

2. The method of claim 1 wherein the nucleic acid samples comprise PCR heteroduplex and homoduplex products.

3. The method of claim 1 wherein in the step of applying the test mixture to a reversed phase support in a denaturing liquid chromatography column, the column is a denaturing high performance liquid chromatography (DHPLC) column.

4. The method of claim 1 wherein each detectable tag comprises a fluorescent dye.

5. The method of claim 4 wherein the step of providing a test mixture comprises the steps of:

combining a different fluorescent dye with each nucleic acid sample to form a labeled nucleic acid sample; and combining the labeled nucleic acid samples to form a test mixture.

6. The method of claim 5 wherein the step of combining a different fluorescent dye with each nucleic acid sample comprises the step of combining a different fluorescent dye with each nucleic acid sample during polymerase chain reaction amplification of the nucleic acid sample.

7. The method of claim 1 wherein the nucleic acid sample comprises DNA or RNA.

8. The method of claim 1 wherein the step of eluting the test mixture under partially denaturing conditions comprises eluting with a mobile phase comprising an ion-pairing agent and an organic solvent.

9. The method of claim 1 wherein the partially denaturing conditions comprise a temperature of about 50° C. to about 80° C.

10. The method of claim 1 wherein the step of detecting spectrally resolved signals comprises the step of using a spectrophotofluorometric HPLC detector.

11. The method of claim 1 wherein each different tag is a spectrally detectable tag selected from the group of an electromagnetic tag and an electrochemical tag.

12. The method of claim 11 wherein the tag is a spectrally detectable tag selected from the group of a spectrophotometric tag and a spectrofluorometric tag.

13. The method of claim 1 wherein the step of detecting the spectrally resolved signals produced by the nucleic acid samples labeled with the detectable tags comprises the step of passing the separately labeled nucleic acid samples through a detection zone of a detector substantially simultaneously, each sample generating a different specific signal which is spectrally resolved from the different specific signals of the other nucleic acid samples.

14. The method of claim 13 wherein in the step of passing the detector excites the detectable tags at one wavelength and detects emissions at multiple wavelengths.

15. The method of claim 13 wherein in the step of passing the detector excites the detectable tags using zero-order excitation.

16. The method of claim 1, wherein in the step of eluting, the different tags behave similarly in denaturing liquid chromatography.

17. The method of claim 16, wherein the different tags behave similarly by being retainable on the reversed phase support for substantially the same amount of time.

18. The method of claim 1, wherein in the step of eluting, the different tags do not substantially interfere with nucleic acid sample denaturation and separation.

19. The method of claim 18, wherein the different tags do not substantially interfere with denaturation by not substantially perturbing the denaturation conditions of the nucleic acid samples, and wherein the different tags do not substantially interfere with separation by not substantially perturbing chromatographic retention characteristics of the nucleic acid samples.

* * * * *

(12) EX PARTE REEXAMINATION CERTIFICATE (4985th)
United States Patent
Apffel, Jr. et al.

(10) Number: US 6,379,889 C1
(45) Certificate Issued: Aug. 31, 2004

(54) MULTIPLEXING METHODS FOR IDENTIFYING NUCLEIC ACIDS USING DENATURING LIQUID CHROMATOGRAPHY

(75) Inventors: James A. Apffel, Jr., Mountain View, CA (US); Karen M. Hahnenberger, Cupertino, CA (US); Mel N. Kronick, Palo Alto, CA (US); Martin Verhoef, Redwood City, CA (US)

(73) Assignee: Agilent Technologies, Santa Clara, CA (US)

Reexamination Request:
No. 90/006,391, Sep. 26, 2002

Reexamination Certificate for:
Patent No.: 6,379,889
Issued: Apr. 30, 2002
Appl. No.: 09/434,035
Filed: Nov. 4, 1999

(51) Int. Cl.[7] .......................... C12Q 1/68; G01N 33/00; C07H 21/02
(52) U.S. Cl. .............................. 435/6; 436/94; 436/172; 436/800; 436/805; 536/23.1; 536/24.3; 536/25.3
(58) Field of Search ...................... 435/6, 91; 536/22.1, 536/23.1, 24.2, 24.33, 25.4; 436/94, 171, 172, 150, 161, 163, 177, 800, 805, 806, 904, 905

(56) References Cited

U.S. PATENT DOCUMENTS

| | | | |
|---|---|---|---|
| 4,683,195 A | | 7/1987 | Mullis et al. |
| 4,811,218 A | | 3/1989 | Hunkapiller et al. |
| 5,171,534 A | | 12/1992 | Smith et al. |
| 5,741,411 A | | 4/1998 | Yeung et al. |
| 5,763,181 A | * | 6/1998 | Han et al. ................. 435/6 |
| 5,772,889 A | * | 6/1998 | Gjerde et al. ............. 210/635 |
| 5,789,153 A | | 8/1998 | Falkner et al. |
| 5,795,976 A | | 8/1998 | Oefner et al. |
| 5,994,076 A | | 11/1999 | Chenchik et al. |

| | | | |
|---|---|---|---|
| 6,210,885 B1 | | 4/2001 | Gjerde et al. |
| 6,361,671 B1 | * | 3/2002 | Mathies et al. ............. 204/452 |
| 2002/0167665 A1 | * | 11/2002 | Yeung et al. ............... 356/344 |

FOREIGN PATENT DOCUMENTS

| | | | |
|---|---|---|---|
| JP | 03175356 | * | 7/1991 |
| WO | WO 97/27325 | * | 7/1997 |
| WO | WO 99/19514 | | 4/1999 |

OTHER PUBLICATIONS

Kim et al. 1995, Eur, J, Biochem. 228:849–854.*
U.S. patent application Ser. No. 60/075,720, Taylor et al., filed Feb. 24, 1998.
O'Donovan et al., "Blind Analysis of Denaturing High–Performance Liquid Chromatography as a Tool for Mutation Detection," Genomics, (1998) vol. 52, pp. 44–49.
Hahnenberger, et al., "Applications of HPLC for NDA Analysis," Microbial & Comparative Genomics 3(3), Abstract B–01 (1998), and copy of the Poster.
Hewlett–Packard Company product literature, "Zorbax Columns—Eclipse dsNDA," Copyright 1998.
Hewlett–Packard Company product literature, Zorbax Eclipse dsNDA Analysis Column,: Copyright 1999.
Liu, et al., "Denaturing High Performance Liquid Chromatography (DHPLC) Used in the Detection of Germline and Somatic Mutations," Nucleic Acids Research, (1998) vol. 20, pp. 1369–1400.
Oefner et al., "High–Resolution Liquid Chromatography of Fluorescent Dye–Labeled Nucleic Acids," Analytical Biochemistry, 233, 39–46 (1994).

(List continued on next page.)

Primary Examiner—Jeffrey Fredman (57) ABSTRACT

A method is provided for the separation of nucleic acid samples. The method includes: providing a test mixture of a plurality of nucleic acid samples, wherein each sample is labeled with a spectrally detectable tag; applying the test mixture to a reversed phase solid support; eluting the mixture under partially denaturing conditions; and detecting spectrally resolved signals produced by the nucleic acid samples labeled with the detectable tags.

OTHER PUBLICATIONS

Oefner, "HPLC in Genetics" abstract from International Symposium on Proteins, Peptides and polynucleotides meeting registration materials (Nov. 11, 1999).

Oefner, et al., "Comparative NDA Sequencing by Denaturing High-performance Liquid chromatography (DHPLC)," Am. J. Hum. Genet. 57(4), Abstract 1547 (1995).

Ophoff, et al., "Familial Hemiplegic Migraine and Episodic Ataxia Type-2 Are Caused by Mutations in the CA2+ Channel Gene CA CNL1A4," Cell, 87(3), 543–552 (1996).

Sarasep, Inc., product literature, "DNASep Startup, Upgrade and Installation Kits—Accessories and Kits for Your HPLC System, to Insure Optimal DNA Analysis" (1995).

Transgenomic, Inc., advertisement, "Analysis of Tumor Heterogeneity at the DNA Level by Automated Fluorescence TMHA Method," copyright 1999.

Transgenomic, Inc., website, "Press: New Wave HS NDA Analysis System Introduced at AACR '99," Jan. 11, 2000.

Transgenomic, Inc., website "Products & Technology: Nucleic Acid Separations—DHPLC Technology," Jan. 11, 2000.

Verpy, et al., "Efficient Detection of Point Mutations on Color-Coded Strands of Target DNA.") Proc. Natl. Acad. Sci., USA, 91, 1873–1877 (1994).

Wagner, et al., "BRCA 1–Related Breast Cancer in Austrian Breast and Ovarian Cancer Families: Specific BRCA 1 Mutations and Pathological Characteristics," Int. J. Cancer, 77, 354–360 (1998).

* cited by examiner

EX PARTE REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

Claims 1–19 are cancelled.

\* \* \* \* \*